(12) United States Patent
Estabrook et al.

(10) Patent No.: US 6,447,488 B2
(45) Date of Patent: *Sep. 10, 2002

(54) APPARATUS FOR THE DIALYSIS OF BLOOD, METHOD FOR FABRICATING THE SAME, AND METHOD FOR THE DIALYSIS OF BLOOD

(75) Inventors: Brian K. Estabrook, Foxboro, MA (US); Paul J. Smith, West Kingston, RI (US); Frank R. Prosl, Duxbury; Harold M. Martins, Newton, both of MA (US)

(73) Assignee: Biolink Corporation, Norwell, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/044,372

(22) Filed: Mar. 19, 1998

(51) Int. Cl.$^7$ .......................... A61M 25/00; A61M 37/00
(52) U.S. Cl. .......................... 604/264; 604/502; 604/527
(58) Field of Search .......................... 604/27, 28, 43, 604/4–6, 264, 523–527, 530–532, 4.01, 5.01–6.07

(56) References Cited

U.S. PATENT DOCUMENTS

| | | | | |
|---|---|---|---|---|
| 4,895,561 A | * | 1/1990 | Mahurkar | 604/43 |
| 5,041,098 A | * | 8/1991 | Loiterman et al. | 604/175 |
| 5,190,520 A | * | 3/1993 | Fenton, Jr. et al. | 604/43 |
| 5,221,255 A | * | 6/1993 | Mahurkar et al. | 604/43 |
| 5,221,256 A | * | 6/1993 | Mahurkar | 604/43 |
| 5,279,596 A | * | 1/1994 | Castaneda et al. | 604/282 |
| 5,334,171 A | * | 8/1994 | Kaldany | 604/282 |
| 5,346,471 A | * | 9/1994 | Raulerson | 604/43 |
| 5,348,536 A | * | 9/1994 | Young et al. | 604/43 |
| 5,374,245 A | * | 12/1994 | Mahurkar | 604/43 |
| 5,472,417 A | * | 12/1995 | Martin et al. | 604/43 |
| 5,486,159 A | * | 1/1996 | Mahurkar | 604/4 |
| 5,545,151 A | * | 8/1996 | O'Connor et al. | 604/526 |
| 5,554,139 A | * | 9/1996 | Okajima | 604/526 |
| 5,662,622 A | * | 9/1997 | Gore et al. | 604/282 |
| 5,702,373 A | * | 12/1997 | Samson | 604/282 |
| 5,704,926 A | * | 1/1998 | Sutton | 604/526 |
| 5,718,678 A | * | 2/1998 | Fleming, III | 604/43 |
| 5,807,311 A | * | 9/1998 | Palestrant | 604/28 |
| 6,004,310 A | * | 12/1999 | Bardsley et al. | 604/524 |

* cited by examiner

Primary Examiner—Sharon Kennedy
(74) Attorney, Agent, or Firm—Pandiscio & Pandiscio

(57) ABSTRACT

Improved apparatus for the dialysis of blood, a method for fabricating the same, and an improved method for the dialysis of blood.

33 Claims, 13 Drawing Sheets

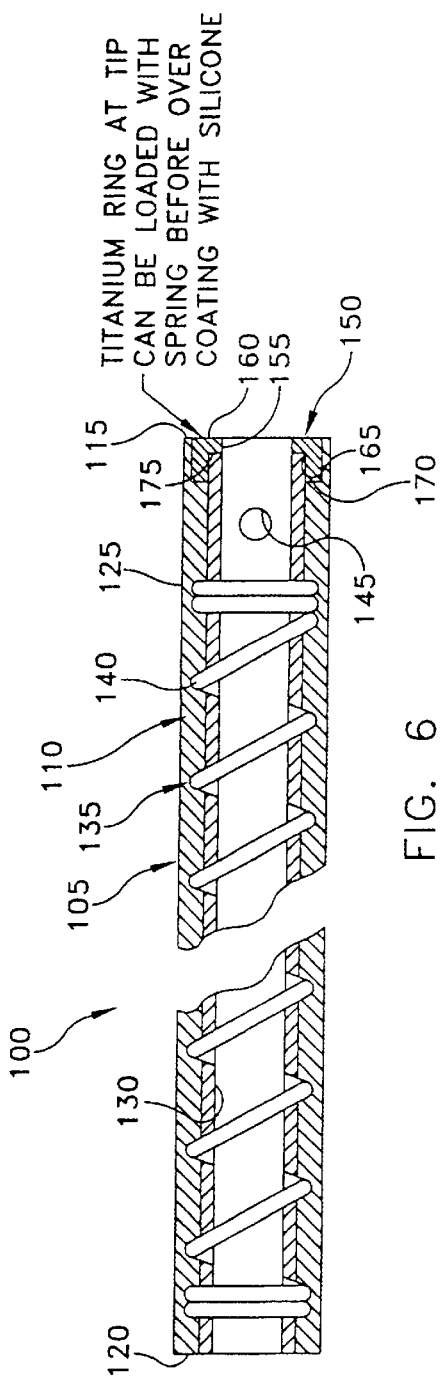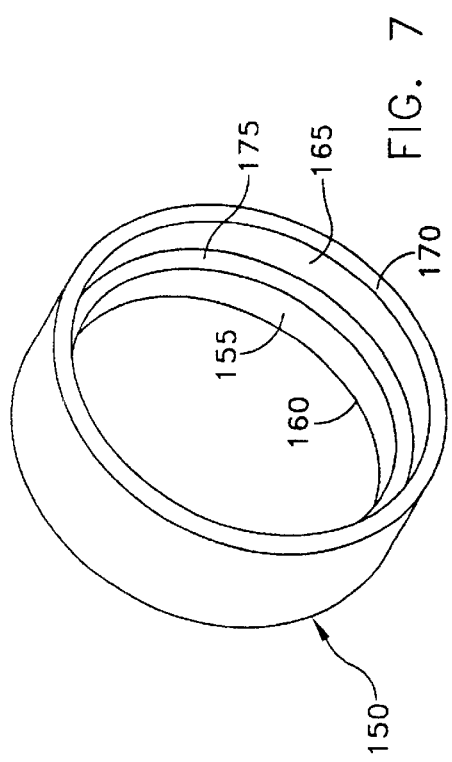
FIG. 6
FIG. 7

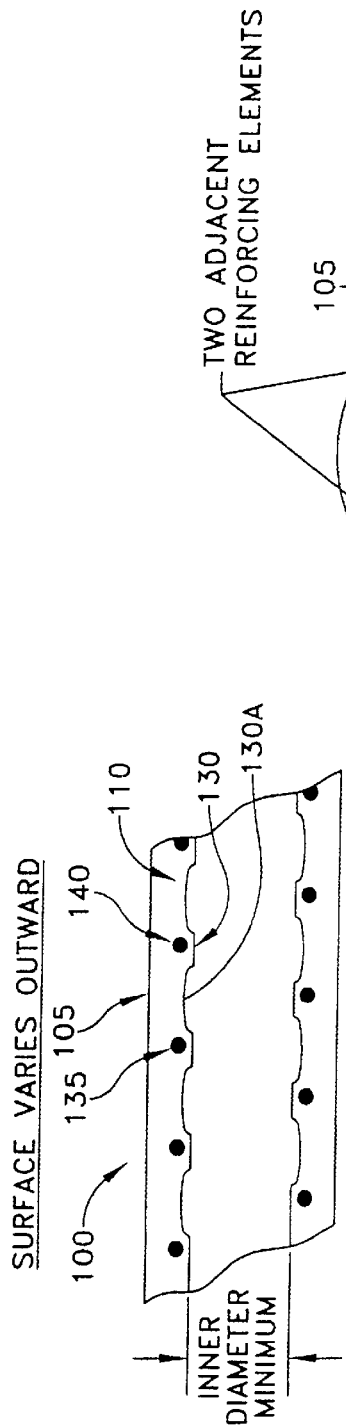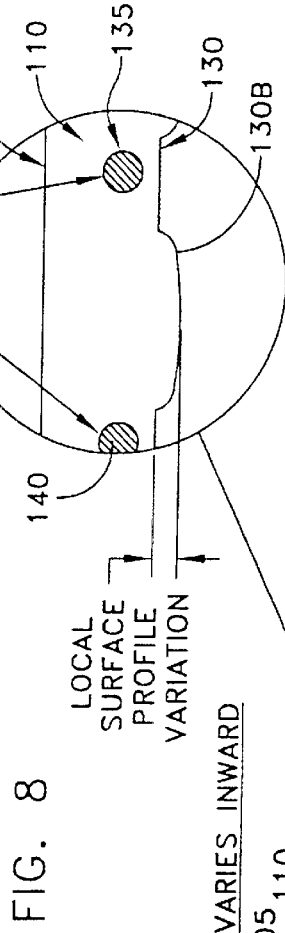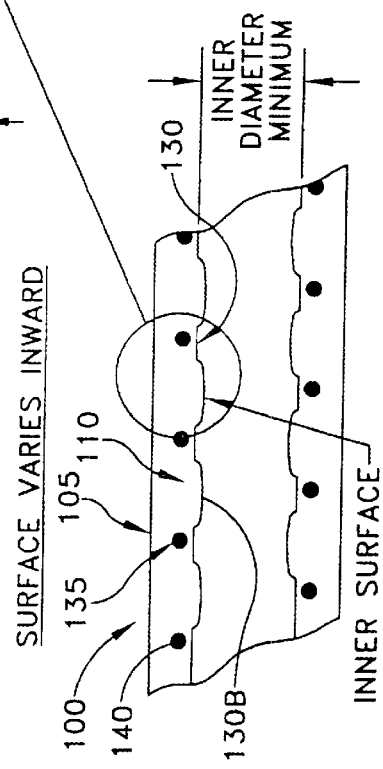

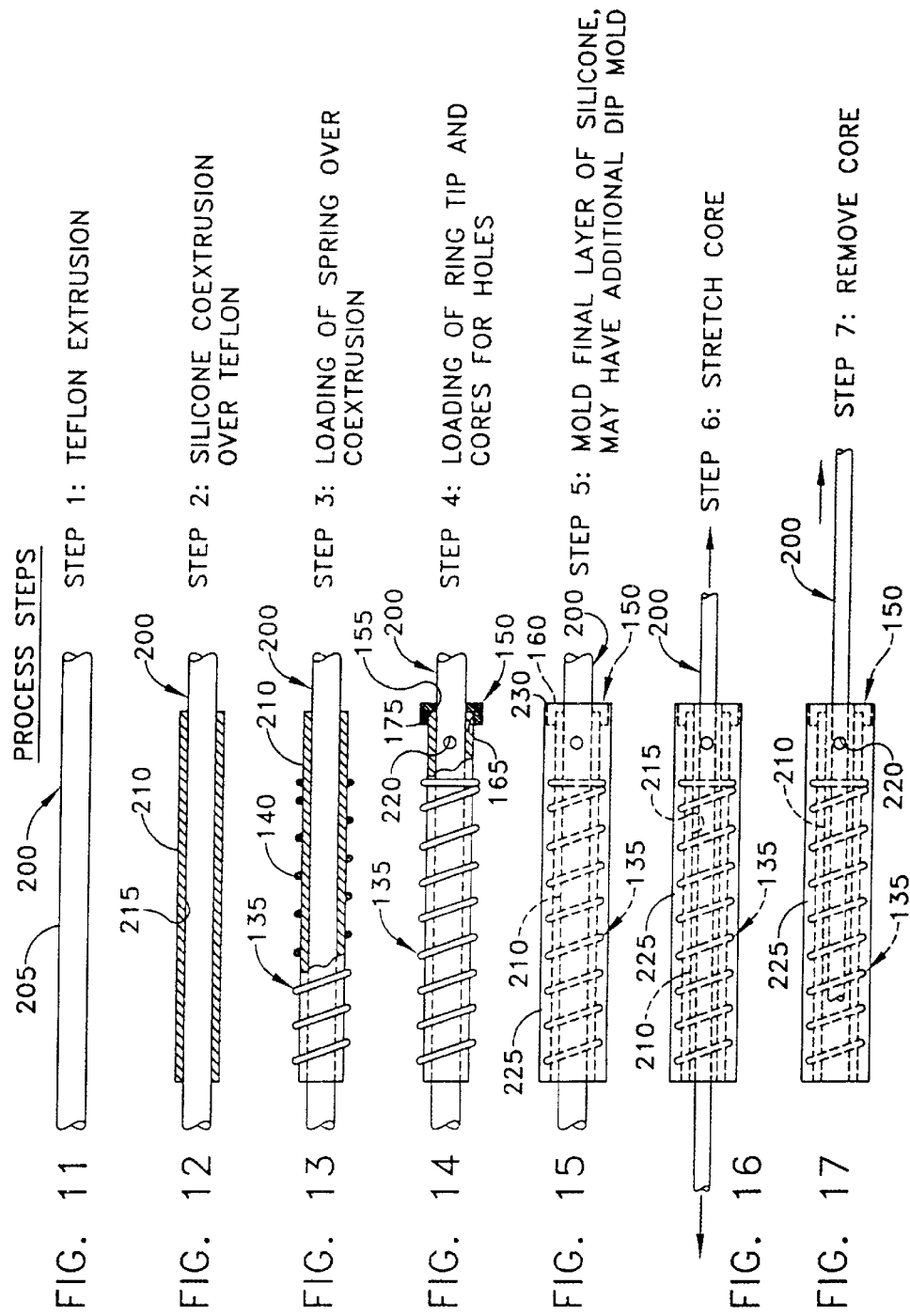

US 6,447,488 B2

APPARATUS FOR THE DIALYSIS OF BLOOD, METHOD FOR FABRICATING THE SAME, AND METHOD FOR THE DIALYSIS OF BLOOD

FIELD OF THE INVENTION

This invention relates to the dialysis of blood in general, and more particularly to apparatus and methods for use in the same.

BACKGROUND OF THE INVENTION

A healthy kidney removes toxic wastes and excess water from the blood. In End Stage Renal Disease ("ESRD"), or chronic kidney failure, the kidneys progressively stop performing these essential functions over a long period of time. When the kidneys fail, a patient dies within a short period of time unless that patient receives dialysis treatment for the rest of that patient's life or undergoes transplantation of a healthy, normal kidney. Since relatively few kidneys are currently available for transplantation, the overwhelming majority of patients with ESRD receive dialysis treatment.

Hemodialysis therapy is an extracorporeal (i.e., outside the body) process which removes toxins and water from a patient's blood. A hemodialysis machine pumps blood from the patient, through a dialyzer, and then back to the patient. The dialyzer removes the toxins and water from the blood by a membrane diffusion process. Typically, a patient with chronic kidney disease requires hemodialysis three times per week, for 3–6 hours per session. Removing blood from the body requires a vascular access to the patient's blood system.

One common method for accessing a patient's blood system for hemodialysis involves the use of a percutaneous catheter assembly. The percutaneous catheter assembly is inserted into a major vein, such as the femoral, subclavian or jugular vein. For long term maintenance dialysis, the jugular vein is generally the preferred insertion site. The catheter assembly is percutaneous, with one end external to the body and the other end dwelling in either the superior vena cava or the right atrium of the heart. The external portion of the catheter assembly has connectors permitting attachment of blood lines leading to and from the hemodialysis machine.

FIGS. 1 and 2 show the traditional manner of positioning a percutaneous catheter assembly 5 relative to the body. More particularly, percutaneous catheter assembly 5 generally comprises a catheter portion 10 comprising a dual-lumen catheter element 15, and a connector portion 20 comprising an extracorporeal connector element 25. The catheter assembly's extracorporeal connector element 25 is disposed against the chest 30 of the patient, and the distal end 35 of catheter element 15 is passed into the patient's internal jugular vein 40 (FIG. 2) and then down into the patient's superior vena cava 45. More particularly, the distal end 35 of catheter element 15 is positioned within the patient's superior vena cava 45 such that the mouth 50 of suction line 55, and the mouth 60 of return line 65, are both located between the patient's right atrium 70 and the patient's left subclavia vein 75 and right subclavia vein 80. Alternatively, the distal end 35 of catheter element 15 may be positioned so that mouth 50 of suction line 55, and mouth 60 of return line 65, are located within the patient's right atrium 70. The percutaneous catheter assembly 5 is then left in this position relative to the body, waiting to be used during an active dialysis session.

When hemodialysis is to be performed on the patient, the catheter assembly's extracorporeal connector element 25 is appropriately connected to a dialysis machine (not shown), i.e., suction line 55 is connected to the input port (i.e., the suction port) of the dialysis machine, and return line 65 is connected to the output port (i.e., the return port) of the dialysis machine. The dialysis machine is then activated (i.e., the dialysis machine's blood pump is turned on and the flow rate set), whereupon the dialysis machine will withdraw relatively "dirty" blood from the patient through suction line 55 and return relatively "clean" blood to the patient through return line 65.

It has also been proposed to use a subcutaneous port and catheter assembly to provide vascular access for hemodialysis.

More particularly, a subcutaneous port and catheter assembly 82 is shown in FIGS. 3–5. Looking first at FIG. 3, subcutaneous port and catheter assembly 82 generally comprises a connector portion 84 comprising a subcutaneous port element 86, and the aforementioned catheter portion 10 comprising the dual-lumen catheter element 15. As noted above, the catheter element 15 in turn comprises the suction line 55 and the return line 65. Subcutaneous port element 86 includes a needle port 88 which is connected to suction line 55, and a needle port 90 which is connected to return line 65. The distal end of suction line 55 terminates in the aforementioned mouth 50, and the distal end of return line 65 terminates in the aforementioned mouth 60.

FIGS. 4 and 5 show subcutaneous port and catheter assembly 82 positioned within the body. More particularly, the assembly's port element 86 is disposed under the skin of the patient (e.g., in the chest area of the patient), and the assembly's catheter element 15 is passed into the patient's internal jugular vein 40 and then down into the patient's superior vena cava 45. The distal end of the assembly's catheter element 15 may be positioned within the patient's superior vena cava 45 such that mouth 50 of suction line 55, and mouth 60 of return line 65, are both located approximately between the patient's right atrium 70 and the patient's left subclavia vein 75 and right subclavia vein 80. Alternatively, the distal end of catheter element 15 may be positioned so that mouth 50 of suction line 55, and mouth 60 of return line 65, are located within the patient's right atrium 70. The subcutaneous port and catheter assembly 82 is then left in this position within the body, waiting to be used during an active dialysis session.

When hemodialysis is to be performed on the patient, the assembly's subcutaneous port element 86 is appropriately connected to a dialysis machine, i.e., needle port 88 is connected to the input port (i.e., the suction port) of the dialysis machine with an appropriate percutaneous needle (not shown), and the assembly's needle port 90 is connected to the output port (i.e., the return port) of the dialysis machine with an appropriate percutaneous needle (not shown). The dialysis machine is then activated, whereupon it will withdraw relatively "dirty" blood from the patient through suction line 55 and return relatively "clean" blood to the patient through return line 65.

It will be appreciated that both percutaneous catheter assembly 5 (FIGS. 1 and 2) and subcutaneous port and catheter assembly 82 (FIGS. 3–5) comprise the catheter portion 10, which in turn comprises the dual-lumen catheter element 15, with the distal end of the catheter element normally dwelling in the patient's vascular system.

Inasmuch as a substantial portion of catheter element 15 dwells in the patient's vascular system (e.g., within internal jugular vein 40 and superior vena cava 45), it is desirable for the catheter element to have the smallest possible outside diameter so as to minimize interference with normal blood flow. At the same time, however, it is also desirable for the catheter element to have the largest possible inside diameter so that maximum dialysis blood flow can be achieved. Thus, from the standpoint of blood flow alone, it is desirable for the catheter element to have the thinnest possible wall thickness.

Unfortunately, however, other considerations also come into effect. For one thing, it is also important that the catheter element have the highest possible burst strength so that it will not fail when passing blood under pressure. In addition, it is also important that the catheter element be able to withstand high negative pressures without collapsing, so that blood can be withdrawn from the body at a rapid rate. Furthermore, it is important that the catheter element be capable of being bent at a substantial angle without kinking, such as, for example, at the point where the catheter element undergoes a large deflection in order to enter internal jugular vein 40 (see FIGS. 1 and 4). These and other considerations tend to significantly limit the degree to which the catheter element's wall thickness can be reduced.

Furthermore, the choice of materials for forming the catheter element is also limited, since the element is typically deployed in the patient's body for substantial periods of time. Currently, silicone rubber is the accepted material for forming catheter elements for use in percutaneous catheter assemblies and subcutaneous port and catheter assemblies.

The foregoing factors have, collectively, tended to limit either (1) the degree to which the outside diameter of the catheter element can be reduced, and/or (2) the degree to which the inside diameter of the catheter element can be enlarged, and/or (3) the rate at which blood can be introduced into the patient's body through the catheter element, and/or (4) the rate at which blood can be withdrawn from the patient's body through the catheter element, and/or (5) the degree to which the catheter element can be bent without kinking.

In U.S. Pat. No. 5,041,098, issued Aug. 20, 1991 to Loiterman et al., it was suggested that a helically wound reinforcement wire could be incorporated into the side wall of the catheter element. Such a suggestion could appear to be advantageous, since it could enable the walls of the catheter element to be made thinner yet stronger.

Unfortunately, in practice, Applicants have found that commercially-available coil-reinforced silicone rubber tubes lack the smooth interior lumen desirable for hemodialysis applications.

More particularly, Applicants have discovered that in hemodialysis applications, smooth lumen walls are important for (1) providing the laminar blood flows required for high volume blood transfer, (2) avoiding the creation of irregular blood currents and the creation of blood stagnation areas, (3) avoiding the formation of blood clots, (4) eliminating breeding areas for bacteria, and (5) facilitating flush-cleaning of the apparatus after dialysis has taken place.

Unfortunately, Applicants have also found that commercially-available coil-reinforced silicone rubber tubes lack the smooth interior lumen desirable for hemodialysis applications.

It is believed that this may be due to the facts that (1) commercially-available coil-reinforced silicone rubber tubes are generally used for purposes other than dialysis applications, and (2) the importance of smooth interior lumens has not yet been discovered by the dialysis industry.

It is also believed that commercially-available coil-reinforced silicone rubber tubes may lack the smooth interior lumen desirable for hemodialysis applications due to the manner in which such tubes are typically formed.

More particularly, it is believed that commercially-available coil-reinforced silicone rubber tubes are generally formed by (1) creating an outer tube out of silicone rubber, (2) forcing that tube open, (3) inserting the coil spring inside the forced-open silicone rubber tube, (4) releasing the outer tube so that it contracts back on the coil spring, and (5) dip molding an interior layer of silicone rubber onto the spring and the interior lumen of the outer tube. While such a process is generally adequate for capturing the coil spring within a body of silicone rubber material, it also results in an undulating interior lumen, since the process essentially covers the coil spring and the interior lumen of the outer tube with a substantially constant-thickness dip layer. Coil-reinforced silicone rubber tubes formed with the aforementioned process are not smooth enough for good hemodialysis applications.

OBJECTS OF THE INVENTION

Accordingly, one object of the present invention is to provide improved apparatus for use in the dialysis of blood.

Another object of the present invention is to provide an improved catheter element for use in the dialysis of blood, wherein the catheter element may be used in either a percutaneous catheter assembly or a subcutaneous port and catheter assembly.

And another object of the present invention is to provide an improved catheter element which has the largest possible interior diameter and the smallest possible exterior diameter, yet is resistant to bursting, collapse and kinking.

Still another object of the present invention is to provide an improved catheter element which incorporates reinforcing means within the side wall of the catheter, yet has an interior lumen which is sufficiently smooth that the catheter element may be used in hemodialysis applications with good results.

And another object of the present invention is to provide a support structure at the distal end of the catheter element to help maintain openness of the flow path through the catheter element.

Yet another object of the present invention is to provide an improved method for fabricating apparatus for use in the dialysis of blood.

And another object of the present invention is to provide an improved method for the dialysis of blood.

SUMMARY OF THE INVENTION

These and other objects are addressed by the present invention, which comprises improved apparatus for the dialysis of blood, a method for making the same, and an improved method for the dialysis of blood.

In one preferred embodiment, the present invention comprises a catheter comprising at least one flexible tubular element, the at least one tubular element having an open proximal end, an open distal end and a side wall defining a lumen extending between the open proximal end and the open distal end, the side wall (1) being formed of a biocompatible material, (2) encasing reinforcing means therein for reinforcing the side wall, and (3) having a smooth interior surface for defining the lumen, the smooth interior surface being sufficiently smooth that the at least one tubular element may be used for hemodialysis applications with good results.

In another preferred embodiment, the present invention comprises apparatus for use in the dialysis of the blood of a patient, the apparatus comprising a connector portion and a catheter portion; the connector portion comprising an outlet adapted for communication with a line connected to the input port of a dialysis machine, and an inlet adapted for communication with a line connected to the output port of a dialysis machine; and the catheter portion comprising a catheter element comprising: a suction line and a return line, each such line comprising a flexible tubular element, the tubular element having an open proximal end, an open distal end and a side wall defining a lumen extending between the open proximal end and the open distal end, the side wall (1) being formed of a biocompatible material, (2) encasing reinforcing means therein for reinforcing the side wall, and (3) having a smooth interior surface for defining the lumen, the smooth interior surface being sufficiently smooth that the tubular element may be used for hemodialysis applications with good results; the proximal end of the suction line being connected to the connector portion and in communication with the outlet, and the distal end of the suction line terminating in a suction line mouth; the proximal end of the return line being connected to the connector portion and in communication with the inlet, and the distal end of the return line terminating in a return line mouth; the suction line and the return line being adapted for disposition within the body of the patient so that the suction line mouth and the return line mouth are both disposed in the vascular system of the patient.

In yet another preferred embodiment, the present invention comprises a method for making a catheter, the method comprising the steps of: (a) providing an elongated, removable molding core; (b) forming a tubular element of biocompatible material on the molding core; (c) positioning reinforcing means for reinforcing the tubular element on the outer surface of the tubular element; (d) forming an overlayer of biocompatible material over the tubular element and the reinforcing means; and (e) removing the molding core from the coated tubular element.

In another preferred embodiment, the present invention comprises a method for the dialysis of the blood of a patient, the method comprising the steps of:

(a) providing a dialysis machine, and providing apparatus comprising a connector portion and a catheter portion; the connector portion comprising an outlet adapted for communication with a line connected to the input port of the dialysis machine, and an inlet adapted for communication with a line connected to the output port of the dialysis machine; and the catheter portion comprising a catheter element comprising: a suction line and a return line, each such line comprising a flexible tubular element, the tubular element having an open proximal end, an open distal end and a side wall defining a lumen extending between the open proximal end and the open distal end, the side wall (1) being formed of a biocompatible material, (2) encasing a reinforcing means therein for reinforcing the side wall, and (3) having a smooth interior surface for defining the lumen, the smooth interior surface being sufficiently smooth that the tubular element may be used for hemodialysis applications with good results; the proximal end of the suction line being connected to the connector portion and in communication with the outlet, and the distal end of the suction line terminating in a suction line mouth; the proximal end of the return line being connected to the connector portion and in communication with the inlet, and the distal end of the return line terminating in a return line mouth; the suction line and the return line being adapted for disposition within the body of the patient so that the suction line mouth and the return line mouth are both disposed in the vascular system of the patient;

(b) placing the suction line mouth and the return line mouth in the vascular system of the patient;

(c) connecting the outlet to the input port of the dialysis machine, and connecting the inlet to the output port of the dialysis machine; and (d) operating the dialysis machine.

BRIEF DESCRIPTION OF THE DRAWINGS

These and other objects and features of the present invention will be more fully disclosed or rendered obvious by the following detailed description of the preferred embodiments of the invention, which are to be considered together with the accompanying drawings wherein:

FIG. 6 is a schematic view, partially in section, of novel catheter apparatus formed in accordance with the present invention;

FIG. 7 is a perspective view of a support structure incorporated into the novel catheter apparatus shown in FIG. 6;

FIGS. 8–10 are schematic views illustrating how the local surface profile of the central lumen of the catheter apparatus may vary along the length of the lumen;

FIGS. 11–17 illustrate process steps for fabricating the novel catheter apparatus shown in FIG. 6;

DETAILED DESCRIPTION OF THE PREFERRED EMBODIMENTS

Figure 1:
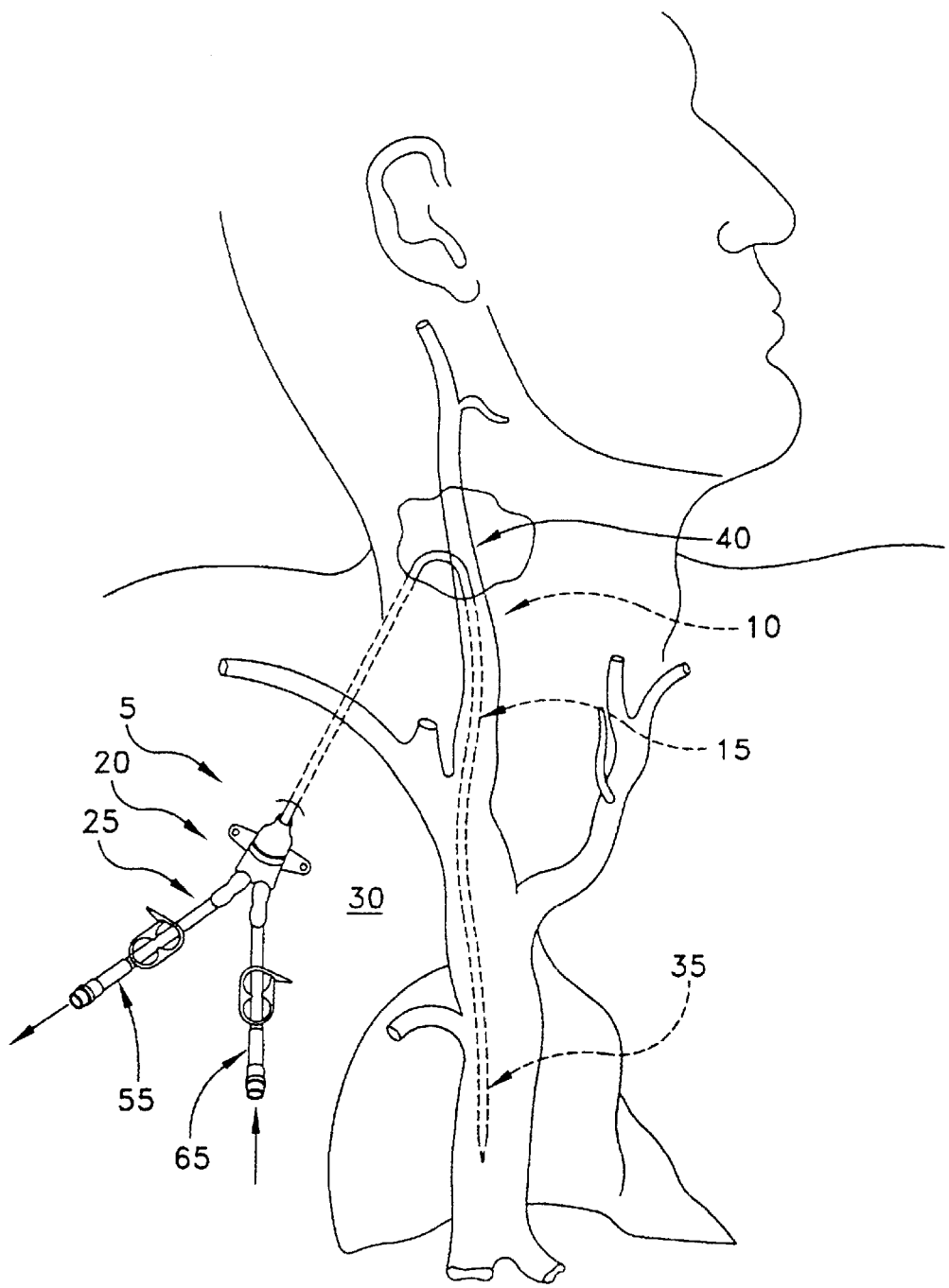
FIG. 1 is a schematic view of a percutaneous catheter assembly installed in a patient.

Looking next at FIG. 6, novel catheter apparatus 100 is shown. Catheter apparatus 100 comprises a silicone rubber tube 105 having a side wall 110, a distal end wall 115 and a proximal end wall 120. The outer surface 125 of side wall 110 has a smooth configuration so as to minimize interference with blood flow when catheter apparatus 100 is disposed in the vascular system of a patient.

A central lumen 130 extends between distal end wall 115 and proximal end wall 120. Central lumen 130 has a smooth interior surface so that blood can be passed through that lumen during a hemodialysis session with good results.

Catheter apparatus 100 also comprises reinforcing means 135 encapsulated within side wall 110 for reinforcing the side wall. In one preferred form of the invention, reinforcing means 135 comprise a coil spring 140. Reinforcing means 135 may extend along the entire length of tube 105, or reinforcing means 135 may extend along only one or more selected portions of tube 105, as preferred. For example, reinforcing means 135 might extend along only an intermediate portion of tube 105. In one form of the invention, reinforcing means 135 are formed out of a radio-opaque material, whereby catheter apparatus 100 may be visualized while within the body of the patient through the use of appropriate imaging equipment, whereby to aid in the proper deployment of the apparatus within the body.

Preferably, but not necessarily, at least one side opening 145 is formed in side wall 110 adjacent to, but spaced from, distal end wall 115. The at least one side opening 145 communicates with central lumen 130, whereby blood may enter and/or exit the distal end of catheter apparatus 100 via either the distal end of central lumen 130 and/or the at least one side opening 145. Preferably the at least one side opening 145 is in the form of a substantially circular hole.

And preferably, but not necessarily, a support structure 150 (FIGS. 6 and 7) is disposed at the intersection of central lumen 130 and distal end wall 115 so as to provide a stiffening element at the distal end of catheter apparatus 100. This member can help maintain openness of the flow path through catheter apparatus 100. In one form of the invention, shown in FIGS. 6 and 7, support structure 150 is formed with a cylindrical configuration, with a bore 155 opening on the support structure's distal end surface 160, a counterbore 165 opening on the support structure's proximal end surface 170, and with an annular shoulder 175 formed at the intersection of bore 155 and counterbore 165. In one preferred form of the invention, support structure 150 is mounted to the distal end of tube 105 so that the support structure's distal end surface 160 lies flush with the tube's distal end surface 115, and so that the support structure's bore 155 is aligned with the tube's central lumen 130 (FIG. 6).

In one preferred form of the invention, tube 105 is formed out of 80 durometer silicone rubber, and has an outside diameter of approximately 0.135 inch, an inside diameter of approximately 0.105 inch, and a wall thickness of approximately 0.015 inch; and coil spring 140 is formed out of titanium, with the wire forming the coil spring being approximately 0.006 inch thick and having a coil rate of approximately 0.031–0.038 pitch. Support structure 150 is preferably formed out of a radio-opaque material, whereby the distal end of catheter apparatus 100 may be visualized while within the body of the patient through the use of appropriate imaging equipment, whereby to aid in the proper deployment of the apparatus within the body.

It is an important feature of the present invention that central lumen 130 be formed smooth enough that catheter apparatus 100 may be used for hemodialysis applications with good results. However, the presence of reinforcing means 135 in the side wall 110 of catheter apparatus 100, and/or the manner of encapsulating reinforcing means 135 within side wall 110, and/or a variety of other factors, may cause variations in the diameter of central lumen 130.

More particularly, as seen in FIG. 8, the presence of reinforcing means 135 may cause central lumen 130 to vary outwardly (as shown at 130A) in the region between adjacent occurrences of reinforcing means 135; or, as seen in FIGS. 9 and 10, the presence of reinforcing means 135 may cause central lumen 130 to vary inwardly (as shown at 130B) in the region between adjacent occurrences of reinforcing means 135. Such variations in the local surface profile of central lumen 130 can have a detrimental effect when catheter apparatus 100 is used for hemodialysis applications.

In accordance with the present invention, central lumen 130 of catheter apparatus 100 is formed smooth enough so that catheter apparatus 100 may be used for hemodialysis applications with good results.

In other words, central lumen 130 of catheter apparatus 100 is formed smooth enough to (1) substantially provide the laminar blood flows required for high volume blood transfer, (2) substantially avoid the creation of irregular blood currents and the creation of blood stagnation areas, (3) substantially avoid the creation of blood clots, (4) substantially eliminate breeding areas for bacteria, and (5) facilitate flush-cleaning of catheter apparatus 100 after dialysis has taken place.

In one particular aspect of the present invention, Applicants have discovered that the cumulative effects of variations in the local surface profile of central lumen 130 can have a significant detrimental effect on the utility of that lumen for hemodialysis applications.

Applicants have further discovered that good hemodialysis results can be achieved if variations in the local surface profile of central lumen 130 average less than about 0.0015 inch and preferably less than about 0.0005 inch (as measured between adjacent occurrences of reinforcing means 135) along the length of central lumen 130. In other words, if catheter apparatus 100 is constructed with a 20 turn helical element, there will be 19 local variation measuring points along any path of measurement taken parallel to the axis of the apparatus. The measurements at these measuring points are then averaged, whereby to provide an average variation in the local surface profile of central lumen 130. Applicants have determined that good hemodialysis results can be achieved where the average variation in the local surface profile of central lumen 130 is less than about 0.0015 inch, and preferably less than about 0.0005 inch.

Thus, in one preferred form of the invention, catheter apparatus 100 is formed so that the average variation in the local surface profile of central lumen 130 is less than about 0.0015 inch, and preferably less than about 0.0005 inch.

The present invention also includes a novel method for fabricating catheter apparatus 100.

In the preferred embodiment of the invention, the novel catheter apparatus 100 is formed as follows.

First, an elongated molding core 200 is provided (FIG. 11). Molding core 200 is formed so that it is removable from a structure which will be molded over the core, as will hereinafter be discussed. In one preferred form of the invention, molding core 200 is formed so that it has a reducible transverse cross-section, whereby the molding core is removable from a structure which will be molded over the core, as will hereinafter be discussed. Molding core 200 has a polished finish so that its outer surface 205 is smooth and free from burrs and other surface irregularities. In one preferred form of the invention, molding core 200 is formed out of a teflon extrusion which may have its transverse cross-section reduced by stretching it along its longitudinal axis. Preferably the teflon extrusion is formed out of virgin teflon stock which is capable of reducing its diameter by approximately 5–10% when subjected to longitudinal stretching. Preferably the virgin stock is homogenous, so that stretching occurs relatively evenly over the entire body of the teflon.

Next, a silicone rubber element 210 is formed about molding core 200 (FIG. 12). Preferably this is done by co-extruding silicone rubber element 210 about the outer surface 205 of molding core 200. Inasmuch as molding core 200 has a smooth outer surface 205, the inner surface 215 of silicone rubber element 210 will therefore also be smooth and free from burrs and other surface irregularities.

Then reinforcing means 135, preferably in the form of coil spring 140, is loaded over silicone rubber element 210 (FIG. 13).

Next, support structure 150 (FIGS. 6, 7, and 14) is fit over the distal end of molding core 200 and the distal end of silicone rubber element 210. More particularly, support structure 150 is fit over the distal end of molding core 200 and the distal end of silicone rubber element 210 so that the distal end of silicone rubber element 210 rests in counterbore 165 of support structure 150 and against shoulder 175 of support structure 150, and so that molding core 200 extends out through bore 155 of support structure 150 (FIG. 14). One or more side openings 220 are then formed in silicone rubber element 210 (FIG. 14), and corresponding molding pins (not shown) are inserted into the one or more side openings 220.

Next, a silicone rubber overlayer 225 is molded over reinforcing means 135 (e.g., coil spring 140) and silicone rubber element 210 (FIG. 15). Preferably silicone rubber overlayer 225 is applied so that it is seamlessly integrated with silicone rubber element 210. Preferably the distal end surface 230 of silicone rubber overlayer 225 is aligned with the distal end surface 160 of support structure 150. The molding pins (not shown) located in the one or more side openings 220 extend out through silicone rubber overlayer 225.

Once this has been done, molding core 200 is removed.

In one preferred form of the invention, where molding core 200 has a reducible transverse cross-section, the molding core first has its transverse cross-section reduced, causing it to separate away from the inside wall 215 of silicone rubber element 210 (FIG. 16). Then molding core 200 is removed.

And in one preferred form of the invention, where molding core 200 is formed out of a teflon extrusion such that stretching the teflon extrusion longitudinally will cause it to reduce in diameter, molding core 200 is first stretched longitudinally, causing the molding core to separate away from the inside wall 215 of silicone rubber element 210 (FIG. 16). Then molding core 200 is removed (FIG. 17.).

After molding core 200 has been removed, the molding pins located in the one or more side openings 220 are withdrawn, thereby yielding the finished catheter apparatus 100. Alternatively, the molding pins located in the one or more side openings 220 may be withdrawn prior to removing molding core 200.

In one preferred form of the invention, silicone rubber element 210 and silicone rubber overlayer 225 are both formed out of 80 durometer silicone rubber; silicone rubber element 210 has a wall thickness of approximately 0.005 inch; and silicone rubber overlayer 225 has a wall thickness (between adjacent occurrences of reinforcing means 135) of approximately 0.010 inch.

It is to be appreciated that, when fabricating catheter apparatus 100 by means of the foregoing process, silicone rubber element 210 and silicone rubber overlayer 225 together form the side wall 110 of catheter apparatus 100. Furthermore, inasmuch as molding core 200 has a smooth outer surface 205, the inside wall 215 of silicone rubber element 210 (which inside wall 215 defines the central lumen 130 of catheter apparatus 100) also has a smooth profile.

It has been found that, by forming catheter apparatus 100 by means of the foregoing process, the central lumen 130 of that apparatus will have an interior surface which is sufficiently smooth that blood can be passed through that lumen during a hemodialysis session with good results.

Among other things, it has been found that, by forming catheter apparatus 100 by means of the foregoing process, the average variation in the local surface profile of central lumen 130 will be less than about 0.0015 inch, and preferably less than about 0.0005 inch.

Two of the catheter apparatus 100 can be attached together in ways well known in the art so as to form a complete dual-lumen catheter element 15.

Figure 2:
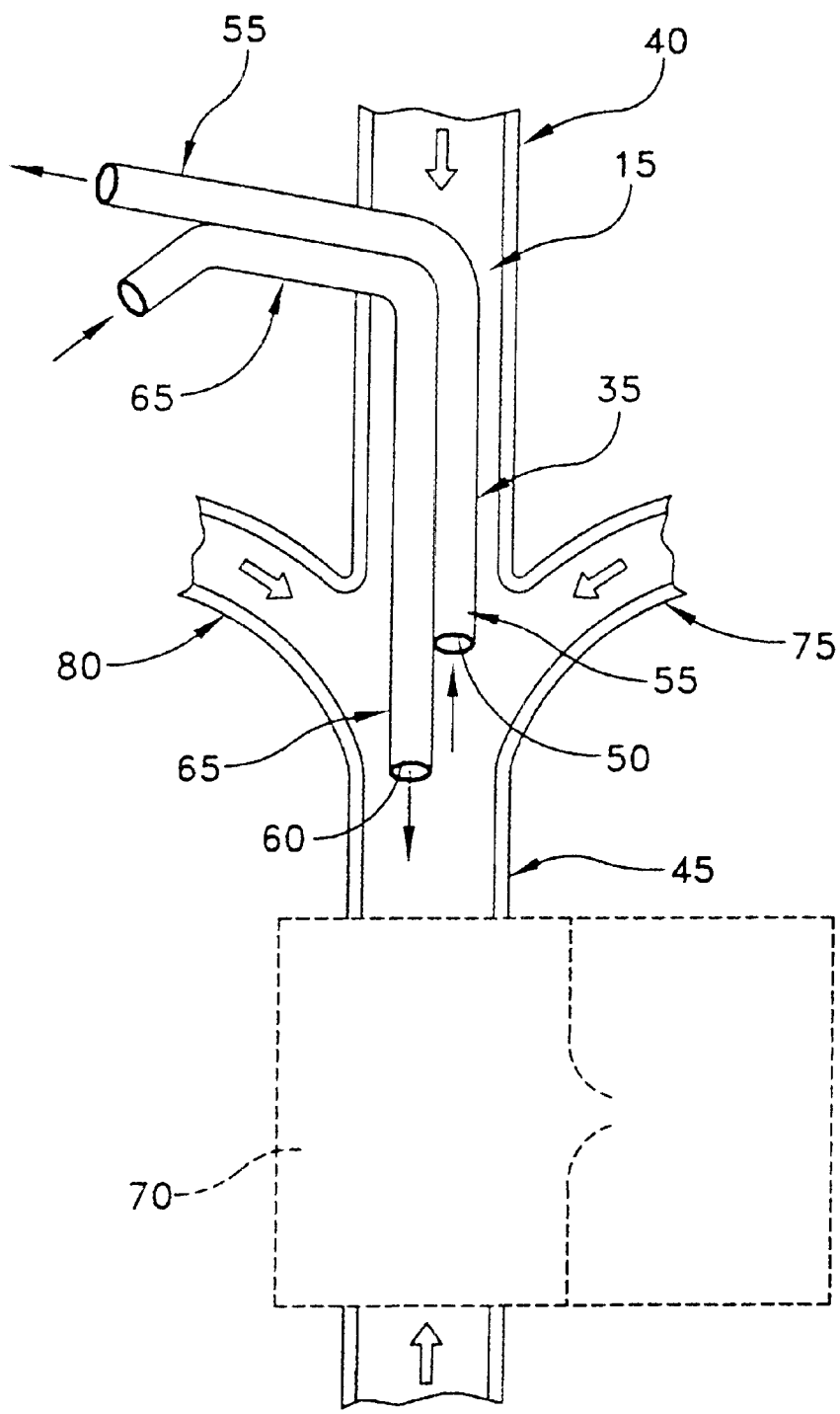
FIG. 2 is a schematic view showing the distal end of the catheter element of the percutaneous catheter assembly of FIG. 1 installed in a patient, with the direction of blood flow being indicated by appropriate arrows.

This complete dual-lumen catheter element 15 can then be combined with the connector portion 20 of a percutaneous catheter assembly so as to form a complete percutaneous catheter assembly such as is schematically shown in FIGS. 1 and 2. Such a percutaneous catheter assembly may then be used in the conventional manner in the hemodialysis of a patient.

Figure 3:
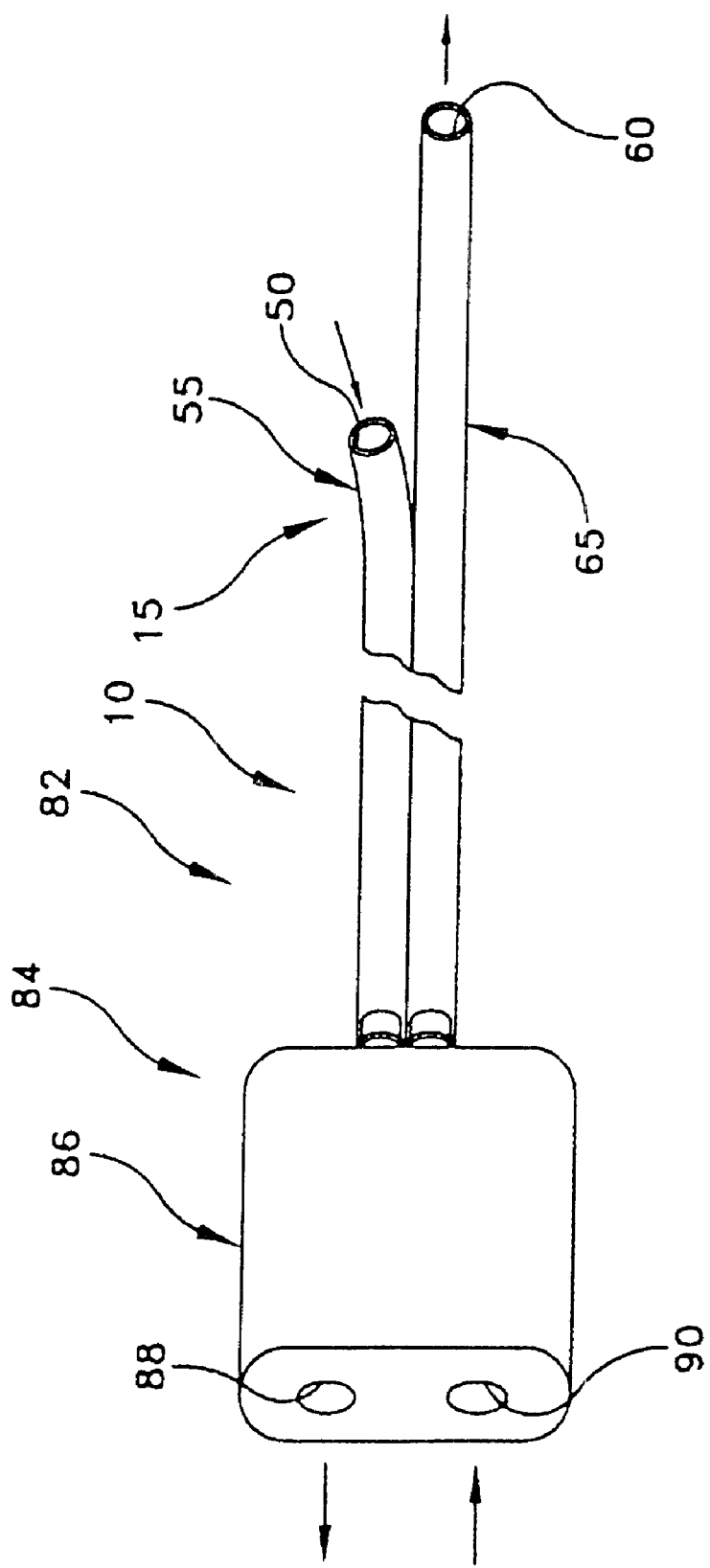
FIG. 3 is a schematic view of a subcutaneous port and catheter assembly.
Figure 4:
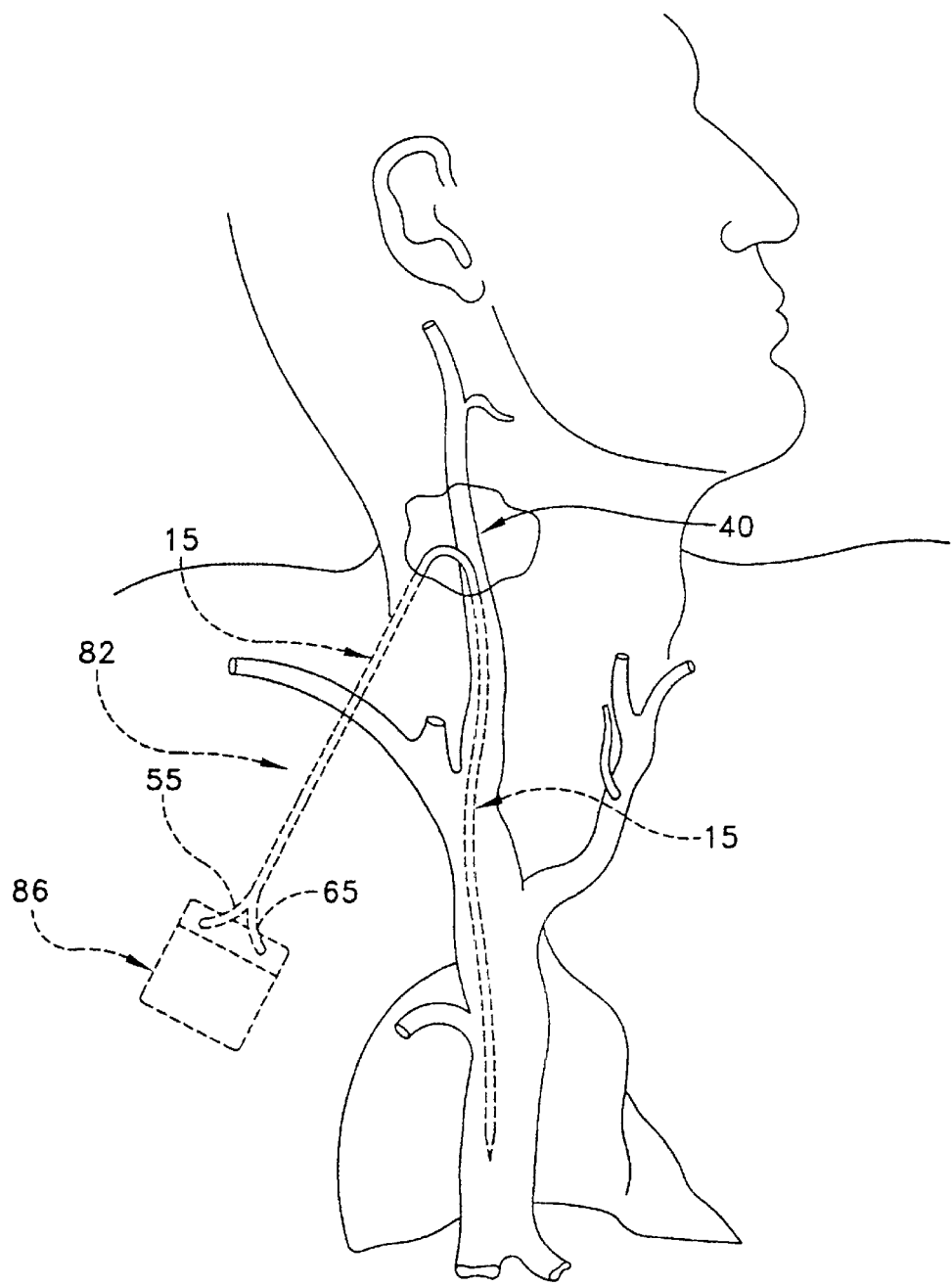
FIG. 4 is a schematic view showing the subcutaneous port and catheter assembly of FIG. 3 installed in a patient.
Figure 5:
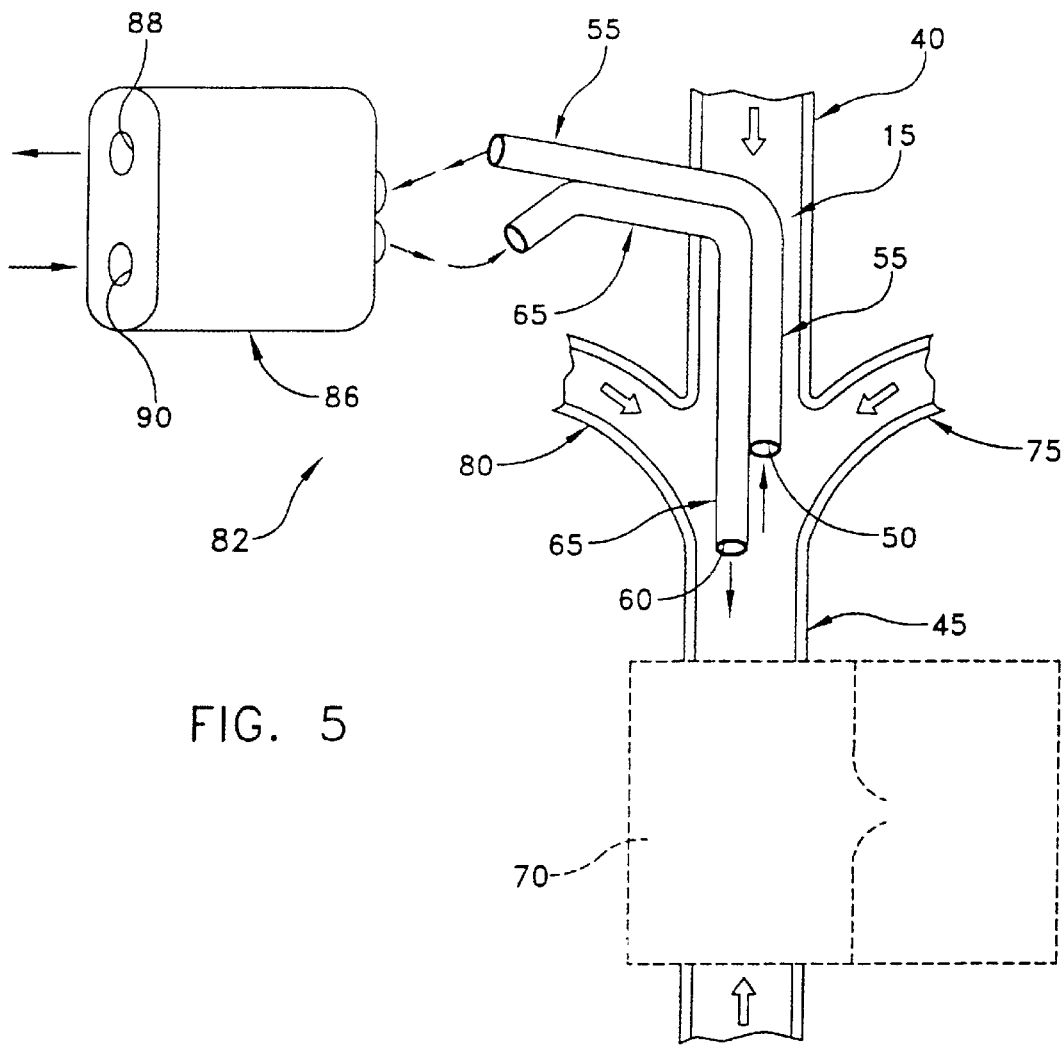
FIG. 5 is an enlarged schematic view showing the subcutaneous port and catheter assembly of FIG. 3 installed in a patient.

Alternatively, the complete dual-lumen catheter element 15 can be combined with the connector portion 84 of a subcutaneous port and catheter assembly so as to form a complete subcutaneous port and catheter assembly such as is schematically shown in FIGS. 3–5. Such a subcutaneous port and catheter assembly may then be used in the conventional manner in the hemodialysis of a patient.

In practice, it has been found possible to provide a dual-lumen catheter element 15, formed out of two of the catheter apparatus 100, which is flexible; capable of substantial bending (e.g., capable of being bent so as to enter the patient's internal jugular vein) without kinking, and resistant to collapse when subjected to substantial negative pressures (e.g., 500 mm of mercury negative pressure).

It should be appreciated that a dual-lumen catheter element 15 formed out of two of the catheter apparatus 100 is easily "field trimmable" to the desired length. In particular, in one preferred trimming method, a scalpel or the like is first used to cut through side wall 110 and expose reinforcing means 135, and then surgical scissors or the like are used to cut through reinforcing means 135. Alternatively, surgical scissors could be used to cut completely through catheter apparatus 100 in a single step.

Numerous modifications can be made to the apparatus and method described above without departing from the scope of the present invention.

Thus, for example, reinforcing means 135 might be formed out of stainless steel, or a hard plastic, or some other material which is harder than the material used to form tube 105.

Or molding core 200 might be formed out of a material other than teflon, where the alternative material is also capable of having its transverse cross-section reduced by longitudinal stretching. Or molding core 200 might have its transverse cross-section reduced by a method other than stretching, e.g., depending on the material involved, the molding core might be melted out or dissolved away so as to separate it from silicone rubber element 210. Furthermore, molding core 200 might be removed from within the molded structure by a technique other than reducing its transverse cross-section. By way of example but not limitation, molding core 200 might comprise a sufficiently lubricious material such that the molding core could be removed from within the molded structure by simply pulling the molding core longitudinally out of the molded structure. Or molding core 200 could be blown out of the molded structure.

Also, if desired, the distal end of catheter apparatus 100 can be formed with an alternative geometry.

Figure 18:
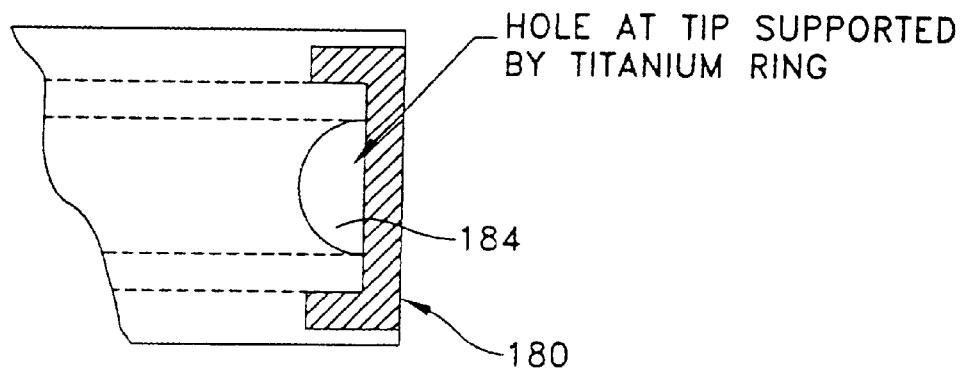
FIG. 18 illustrates the distal end of an alternative form of catheter apparatus formed in accordance with the present invention.
Figure 19:
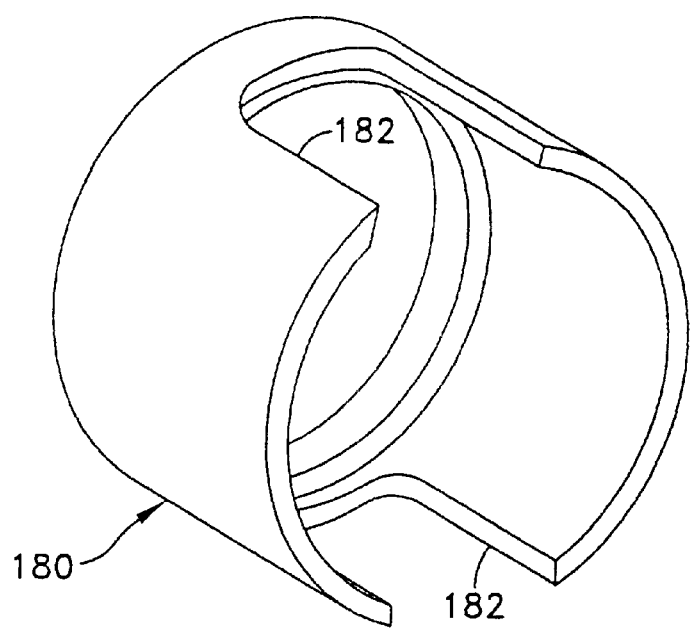
FIG. 19 is a perspective view of the support structure incorporated into the catheter apparatus shown in FIG. 18.

By way of example but not limitation, a support structure 180 (FIGS. 18 and 19) can be utilized, wherein support structure 180 is substantially identical to the support structure 150 discussed above, except that side slots 182 are formed in support structure 180, and appropriate molding pins (not shown) are used in association with side slots 180 to form semi-circular side openings 184 (FIG. 18) in the distal end of the catheter apparatus.

Figure 20:
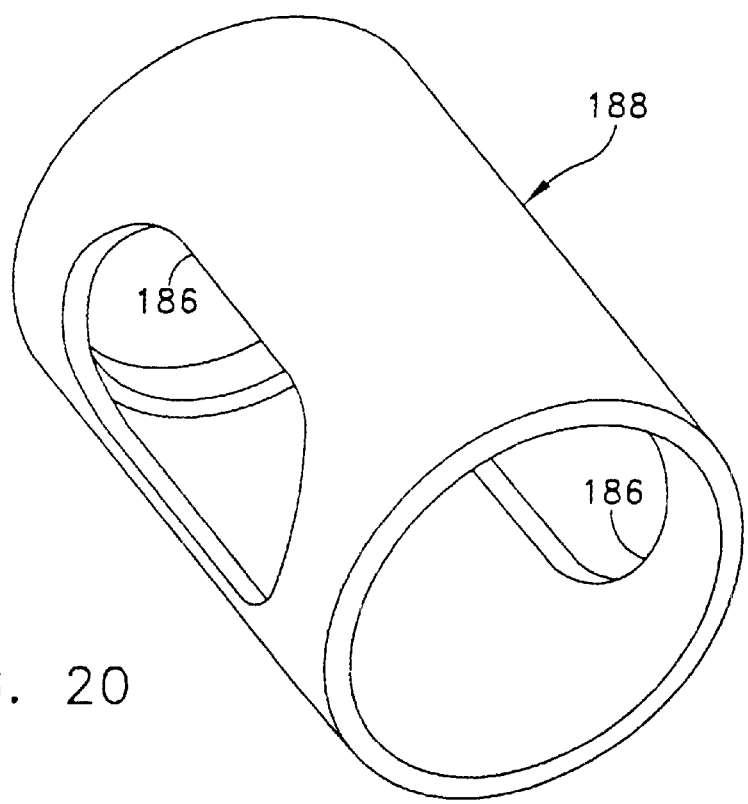
FIGS. 20 and 21 illustrate still other forms of support structures which may be incorporated into catheter apparatus formed in accordance with the present invention.

Or, as seen in FIG. 20, side windows 186 can be formed in a support structure 188 which, when covered with appropriate molding pins during molding, will yield appropriate openings in the distal end of the catheter apparatus.

Figure 21:
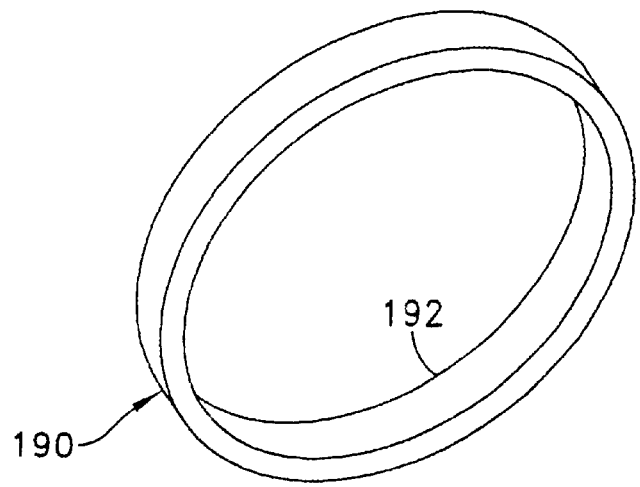
Figure 22:
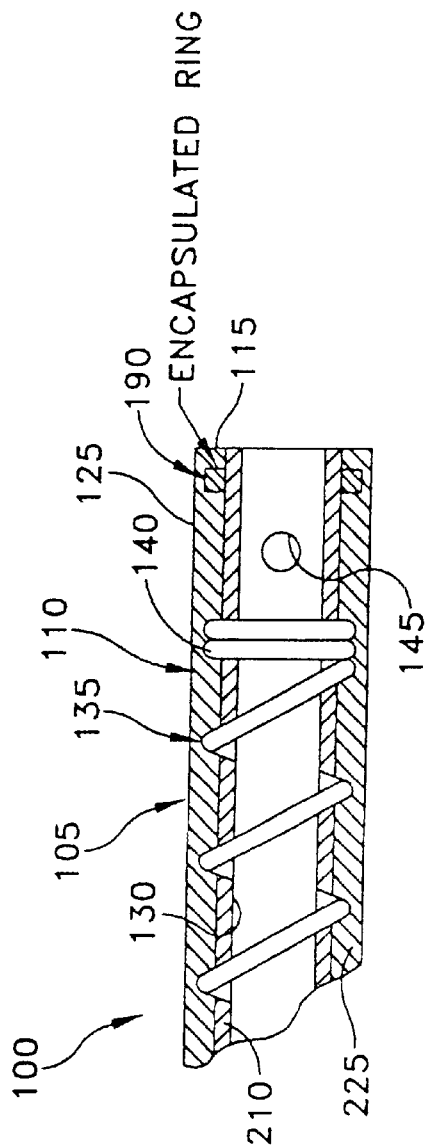
FIG. 22 illustrates an alternative manner for incorporating the support structure of FIG. 21 into catheter apparatus formed in accordance with the present invention.

Or a simple ring-shaped support structure 190 (FIG. 21) can be used, with or without side openings 145. With such a construction, support structure 190 can be positioned so that its distal end surface 192 resides flush with distal end wall 115 of tube 105, in a manner generally analogous to the construction shown in FIG. 6; or support structure 190 can be encapsulated within the distal end of tube 105, in the manner shown in FIG. 22.

It is also possible for the distal support structure to be attached onto a surface of side wall 110 of tube 105, rather than embedded into the material of side wall 110.

And the distal support structure may open on the distal end of tube 105, and/or open on the inner lumen of tube 105, and/or open on the outer lumen of tube 105.

Or the distal support structure may be omitted completely from the catheter apparatus if desired.

Figure 22A:
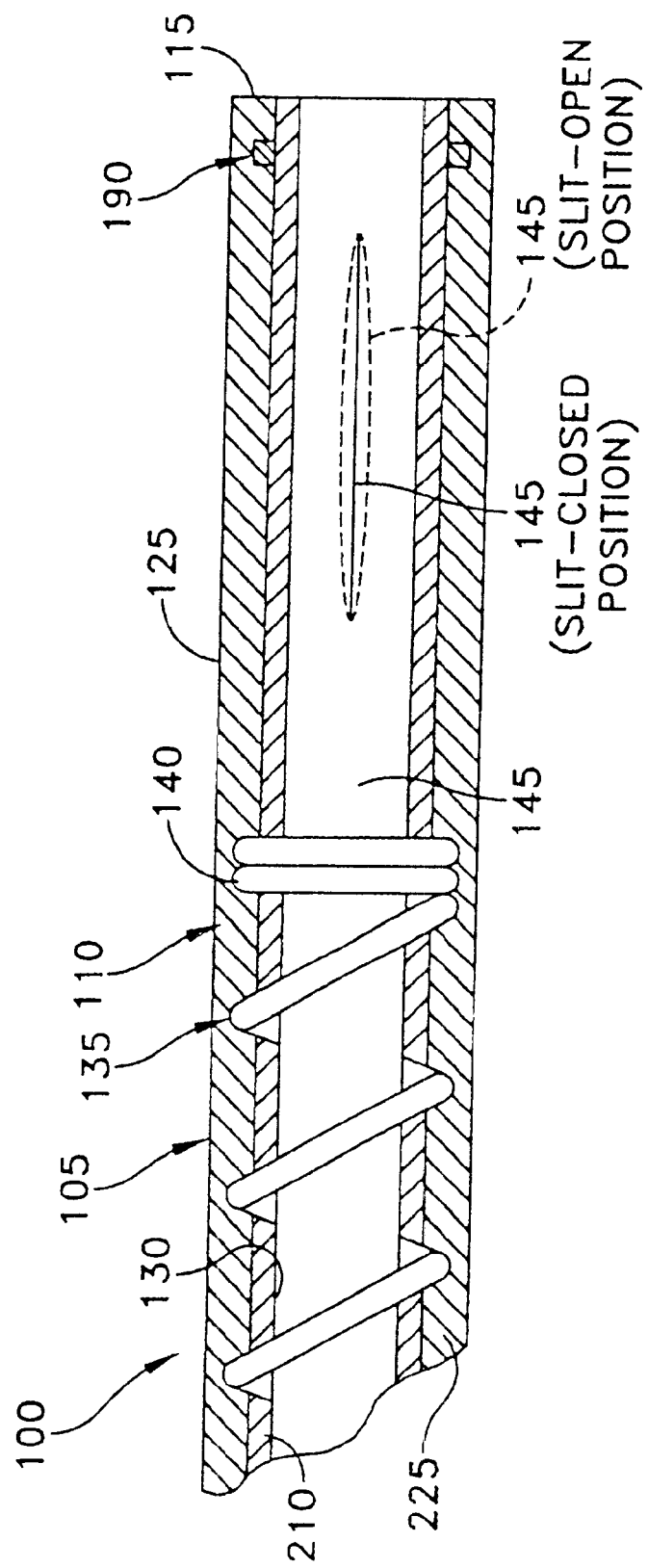
FIG. 22A illustrates an alternative manner for forming side openings near the distal end of the catheter apparatus, wherein the side openings are in the form of relatively narrow, longitudinally-extending slits.

Furthermore, side openings 145 might comprise relatively narrow, longitudinally-extending slits rather than holes, in which case they could act something like a check valve, opening under positive internal pressure but otherwise remaining substantially closed. See, for example, FIG. 22A, which shows side openings 145 in the form of such relatively narrow, longitudinally extending slits, with the slits being shown in their closed position in solid line and in their open position in dashed, or phantom, line.

Figure 23:
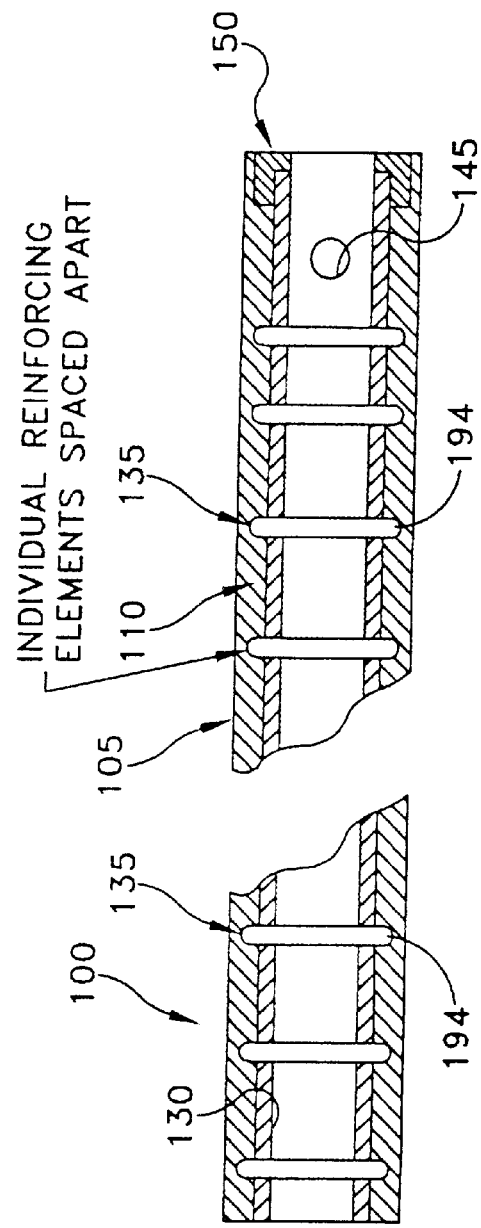
FIG. 23 illustrates catheter apparatus utilizing an alternative form of reinforcing means.
Figure 23A:
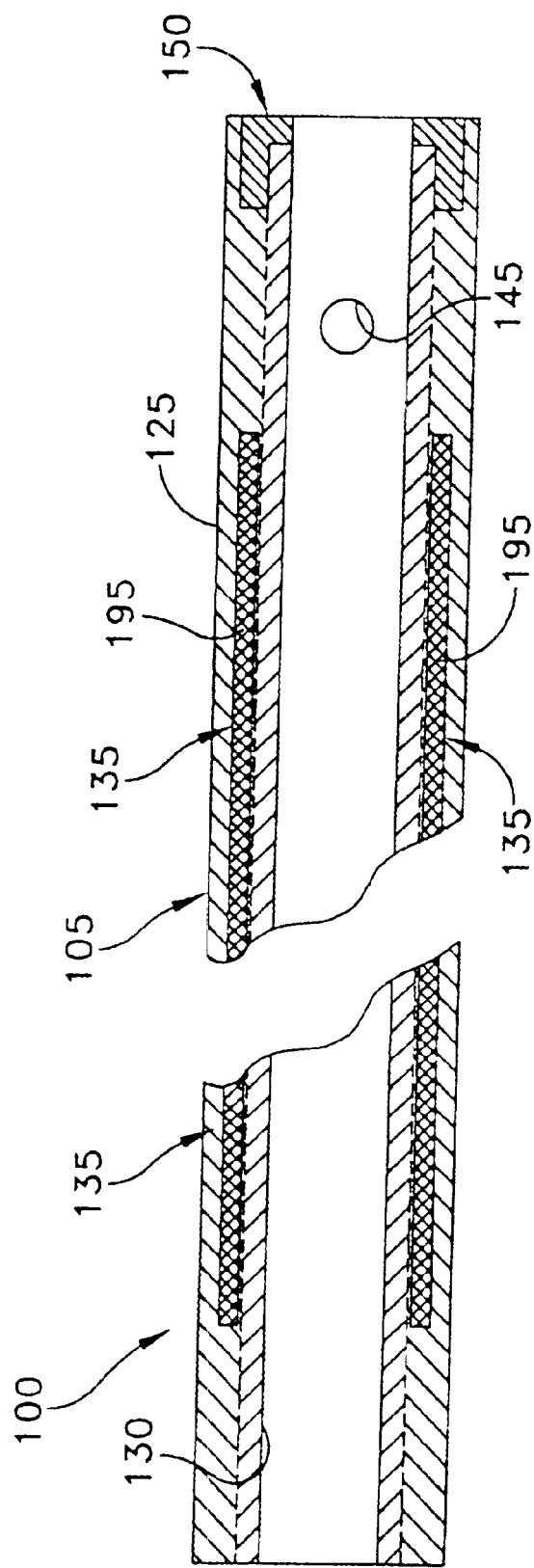
FIG. 23A schematically illustrates an alternative form of reinforcing means, wherein the reinforcing means comprise a tubular, braided mesh reinforcer.

It should also be appreciated that reinforcing means 135 may take a form other than the coil spring 140 discussed above. For example, reinforcing means 135 might take the form of a plurality of ring-like elements 194, such as is shown in FIG. 23. Alternatively, reinforcing means 135 might comprise a tubular, braided mesh reinforcer. See, for example, FIG. 23A, where reinforcing means 135 are shown, schematically, in the form of a tubular, braided mesh reinforcer 195.

It should also be appreciated that one might form a catheter apparatus of the sort generally described above, including a distal support structure, but omitting reinforcing means 135.

It will, of course, be appreciated that various other modifications may be made to the embodiments disclosed above without departing from the spirit and scope of the present invention. Accordingly, it is intended that this invention be limited only by the claims ultimately issued from this patent application and/or from any patent application(s) claiming priority therefrom.

ADVANTAGES OF THE INVENTION

Numerous advantages are achieved through the provision and use of the present invention.

For one thing, the present invention provides improved apparatus for use in the dialysis of blood.

And the present invention provides an improved catheter element for use in the dialysis of blood, wherein the catheter element may be used in either a percutaneous catheter assembly or a subcutaneous port and catheter assembly.

Also, the present invention provides an improved catheter element which has the largest possible interior diameter and the smallest possible exterior diameter, yet is resistant to bursting, collapse and kinking.

And the present invention provides an improved catheter element which incorporates reinforcing means within the side wall of the catheter, yet has an interior lumen which is sufficiently smooth that the catheter element may be used in hemodialysis applications with good results.

The present invention also provides a support structure at the distal end of the catheter element to help maintain openness of the flow path through the catheter element.

Furthermore, the present invention provides an improved method for fabricating apparatus for use in the dialysis of blood.

And the present invention provides an improved method for the dialysis of blood.

Still other advantages associated with the present invention will be obvious to a person skilled in the art.

What is claimed is:

1. A catheter for use in hemodialysis applications comprising at least one flexible tubular element, said at least one flexible tubular element having an open proximal end, an open distal end and a side wall defining a lumen extending between said open proximal end and said open distal end, said lumen being sized large enough for effective use in hemodialysis applications, and said side wall (1) being formed of a soft biocompatible material, (2) encasing a reinforcing means therein for reinforcing said soft biocompatible material so as to prevent said side wall from collapsing under the negative pressures used in the hemodialysis process while still allowing the side wall to undergo the tight bends which can be encountered in hemodialysis applications, and said lumen being substantially surrounded by said reinforcing means along a cross-sectional view thereof, said reinforcing means defining and interior region and an exterior region, said interior region of said reinforcing means consisting of a single lumen, and (3) having a smooth interior surface for defining said lumen, said smooth interior surface being sufficiently smooth that said at least one tubular element may be used for hemodialysis applications with good results.

2. A catheter according to claim 1 wherein the average variation in the local surface profile of said lumen is less than about 0.0015 inch.

3. A catheter according to claim 1 wherein said biocompatible material comprises silicone rubber.

4. A catheter according to claim 3 wherein said biocompatible material comprises silicone rubber having a hardness of approximately 80 durometer.

5. A catheter according to claim 1 wherein said reinforcing means are formed out of a material stiffer than the material used to form said side wall.

6. A catheter according to claim 5 wherein said reinforcing means are formed out of metal.

7. A catheter according to claim 6 wherein said reinforcing means are formed out of titanium.

8. A catheter according to claim 6 wherein said reinforcing means are formed out of stainless steel.

9. A catheter according to claim 5 wherein said reinforcing means are formed out of plastic.

10. A catheter according to claim 1 wherein said reinforcing means comprise a coil spring.

11. A catheter according to claim 10 wherein the wire forming said coil spring has a thickness of approximately 0.006 inch and a coil rate of approximately 0.031–0.038 pitch.

12. A catheter according to claim 10 wherein said coil spring comprises titanium.

13. A catheter according to claim 12 wherein the wire forming said coil spring has a thickness of approximately 0.006 inch and a coil rate of approximately 0.031–0.038 pitch.

14. A catheter according to claim 1 wherein said reinforcing means comprise a plurality of ring-like elements.

15. A catheter according to claim 1 wherein said reinforcing means are formed out of a radio-opaque material.

16. A catheter according to claim 1 wherein said side wall has a thickness of approximately 0.015 inch.

17. A catheter according to claim 1 wherein said at least one side wall comprises a smooth outer surface.

18. A catheter according to claim 1 further comprising a support structure attached to said side wall adjacent to said open distal end of said at least one flexible tubular element.

19. A catheter according to claim 18 wherein said support structure is at least partially embedded in said side wall.

20. A catheter according to claim 16 wherein said support structure is formed out of a radio-opaque material.

21. A catheter according to claim 18 wherein said at least one tubular element is substantially cylindrical, and further wherein said support structure comprises a ring-shaped element formed of a material more rigid than the biocompatible material forming said at least one tubular element.

22. A catheter according to claim 18 wherein said at least one tubular element is substantially cylindrical, and further wherein said support structure comprises a substantially cylindrical element having an outer diameter, a distal end, a proximal end, a first inner diameter portion adjacent to said distal end, a second inner diameter portion adjacent to said proximal end, and a proximally-facing shoulder connecting said first and second inner diameter portions.

23. A catheter according to claim 18 wherein said at least one tubular element is substantially cylindrical, and further wherein said support structure comprises a substantially cylindrical element defining at least one opening therethrough.

24. A catheter according to claim 23 wherein said at least one opening comprises a slot extending to said proximal end of said support structure.

25. A catheter according to claim 1 further comprising a support structure attached to said side wall adjacent to, but spaced from, said open distal end of said at least one flexible tubular element.

26. A catheter according to claim 1 wherein said side wall defines at least one opening therethrough in proximally-spaced, proximate relation to said open distal end of said at least one flexible tubular element.

27. A catheter according to claim 26 wherein said at least one opening comprises a substantially circular hole.

28. A catheter according to claim 26 wherein said at least one opening comprises a longitudinally-extending slit.

29. A catheter according to claim 28 wherein said slit is normally substantially closed, but is capable of opening when a positive internal pressure is established in said lumen.

30. A catheter according to claim 1 wherein said catheter comprises a pair of said flexible tubular elements longitudinally joined together in side-by-side relation to one another.

31. A catheter according to claim 1 wherein said reinforcing means comprise a tubular, braided mesh reinforcer.

32. A catheter for use in hemodialysis applications comprising at least one flexible tubular element, said at least one flexible tubular element having an open proximal end, an open distal end and a side wall defining a lumen extending between said open proximal end and said open distal end, said lumen being sized large enough for effective use in hemodialysis applications, and said side wall being formed of a soft biocompatible material and having a smooth interior surface for defining said lumen, said smooth interior surface being sufficiently smooth that said at least one tubular element may be used for hemodialysis applications with good results, said lumen being substantially surrounded by a reinforcing means along a cross-sectional view thereof, said reinforcing means defining an interior region and an exterior region, said interior region of said reinforcing means consisting of a single lumen, and said catheter further comprising a support structure attached to said wall adjacent to said open distal end of said at least one flexible tubular element.

33. A catheter comprising at least one flexible tubular element, said at least one tubular element having an open proximal end, an open distal end and a side wall defining a lumen extending between said open proximal end and said open distal end, said side wall (1) being formed of a biocompatible material, (2) encasing a reinforcing means therein for reinforcing said side wall, and (3) having a smooth interior surface for defining said lumen, said smooth interior surface being sufficiently smooth that said at least one tubular element may be used for hemodialysis applications with good results;

a support structure attached to said side wall adjacent to said open distal end of said at least one flexible tubular element; and wherein said at least one tubular element is substantially cylindrical, and further wherein said support structure comprises a substantially cylindrical element having an outer diameter, a distal end, a proximal end, a first inner diameter portion adjacent to said distal end, a second inner diameter portion adjacent to said proximal end, and a proximally-facing shoulder connecting said first and second inner diameter portions.

* * * * *